US010372822B2

(12) United States Patent
Devarakonda et al.

(10) Patent No.: US 10,372,822 B2
(45) Date of Patent: Aug. 6, 2019

(54) AUTOMATED TIMELINE COMPLETION USING EVENT PROGRESSION KNOWLEDGE BASE

(71) Applicant: International Business Machines Corporation, Armonk, NY (US)

(72) Inventors: Murthy V. Devarakonda, Peekskill, NY (US); Siddharth A. Patwardhan, Yorktown Heights, NY (US); Preethi Raghavan, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 47 days.

(21) Appl. No.: 15/172,813

(22) Filed: Jun. 3, 2016

(65) Prior Publication Data

US 2017/0351754 A1    Dec. 7, 2017

(51) Int. Cl.
*G06F 17/28* (2006.01)
*G06F 17/27* (2006.01)
(Continued)

(52) U.S. Cl.
CPC ........ *G06F 17/2785* (2013.01); *G06F 16/447* (2019.01); *G06F 16/489* (2019.01);
(Continued)

(58) Field of Classification Search
None
See application file for complete search history.

(56) References Cited

U.S. PATENT DOCUMENTS 9,043,329 B1    5/2015    Patton et al.
9,152,737 B1 *  10/2015    Micali ............... G06F 17/30958
(Continued)

OTHER PUBLICATIONS

Raghavan et al., "Exploring Semi-Supervised Coreference Resolution of Medical concepts using semantic and temporal features", 2012 Conference of the North American Chapter of the Assoc. for Computational linguistics: Human Langage Tech., pp. 731-741, Montreal Canada, Jun. 3-8, 2012.*
(Continued)

*Primary Examiner* — Richard Z Zhu
(74) *Attorney, Agent, or Firm* — Stephen R. Tkacs; Stephen J. Walder, Jr.; Reza Sarbakhsh

(57) ABSTRACT

A mechanism is provided in a computing device configured with instructions executing on a processor of the computing device to implement a timeline generation system, for automated timeline completion. The timeline generation system executing on the processor of the computing device identifies a plurality of events in documents in a corpus of information. The timeline generation system places the plurality of events in a partial timeline data structure. The timeline generation system selects an event progression from an event progression knowledge base. The timeline generation system aligns the selected event progression to the partial timeline data structure. The timeline generation system identifies a set of events missing from the partial timeline data structure. The timeline generation system maps the set of events missing from the partial timeline data structure to the partial timeline based on the selected event progression to form a completed timeline data structure.

14 Claims, 6 Drawing Sheets

(51) Int. Cl.
*G16H 10/00* (2018.01)
*G06F 16/44* (2019.01)
*G06F 16/48* (2019.01)
*G06F 16/9537* (2019.01)
*G06F 16/58* (2019.01)

(52) U.S. Cl.
CPC ......... *G16H 10/00* (2018.01); *G06F 16/5866* (2019.01); *G06F 16/9537* (2019.01)

(56) References Cited

U.S. PATENT DOCUMENTS

| | | | |
|---|---|---|---|
| 9,739,813 B2* | 8/2017 | Houlette | G01R 21/133 |
| 2003/0120458 A1* | 6/2003 | Rao | G06F 17/3061 |
| | | | 702/181 |
| 2006/0168188 A1* | 7/2006 | Dutton | G06Q 10/10 |
| | | | 709/223 |
| 2007/0136296 A1* | 6/2007 | Molesky | G06Q 10/063 |
| 2008/0208631 A1* | 8/2008 | Morita | G06F 19/322 |
| | | | 705/3 |
| 2009/0287678 A1 | 11/2009 | Brown et al. | |
| 2010/0228418 A1* | 9/2010 | Whitlow | G11B 27/105 |
| | | | 701/25 |
| 2011/0040766 A1* | 2/2011 | Robinson | G06F 17/3053 |
| | | | 707/749 |
| 2011/0066587 A1 | 3/2011 | Ferrucci et al. | |
| 2011/0125734 A1 | 5/2011 | Duboue et al. | |
| 2013/0007055 A1 | 1/2013 | Brown et al. | |
| 2013/0018652 A1 | 1/2013 | Ferrucci et al. | |
| 2013/0066886 A1 | 3/2013 | Bagchi et al. | |
| 2013/0159022 A1* | 6/2013 | Verbeek | G06F 19/325 |
| | | | 705/3 |
| 2013/0325787 A1* | 12/2013 | Gerken | G06N 7/005 |
| | | | 706/52 |
| 2014/0006938 A1 | 1/2014 | Black et al. | |
| 2015/0178290 A1* | 6/2015 | Hirooka | G06F 16/447 |
| | | | 715/753 |

OTHER PUBLICATIONS

Bui et al., "Timeline: Visualizing Integrated Patient Records", IEEE Transactions on Information Technology in Biomedicine, vol. 11, No. 4, pp. 462-473, Jul. 2007.*

Chambers, Nathanael et al., "A Database of Narrative Schemas", Proceedings of the Seventh International Conference on Language Resources and Evaluation (LREC'10), http://nlp.stanford.edu/pubs/chambers-lrec2010-schemas.pdf, May 2010, 5 pages.

Chambers, Nathanael et al., "Unsupervised Learning of Narrative Event Chains", Proceedings of ACL-08, http://nlp.stanford.edu/pubs/narrative-chains08.pdf, Columbus, Ohio, Jun. 2008, 9 pages.

Do, Quang X. et al., "Joint Inference for Event Timeline Construction", Proceedings of the 2012 Joint Conference on Empirical Methods in Natural Language Processing and Computational Natural Language Learning (EMNLP-CoNLL '12), Jul. 12, 2012, 11 pages.

Fulda, Johanna, "The Line of Time: Backgrounds and Usage of Event-Timelines", Department of Computer Science, University of British Columbia, Mar. 2013, 13 pages.

High, Rob, "The Era of Cognitive Systems: An Inside Look at IBM Watson and How it Works", IBM Corporation, Redbooks, Dec. 12, 2012, 16 pages.

Hovy, Dirk et al., "When Did that Happen?—Linking Events and Relations to Timestamps", Proceedings of the 13th Conference of the European Chapter of the Association for Computational Linguistics, Avignon, France, Apr. 2012, 9 pages.

Li, Heng et al., "A survey of sequence alignment algorithms for next-generation sequencing", Briefings in Bioinformatics, vol. II, No. 5, May 11, 2010, pp. 473-483.

Mani, Inderjeet et al., "Machine Learning of Temporal Relations", Proceedings of the 21st International Conference on Computational Linguistics and 44th Annual Meeting of the ACL, Sydney, Jul. 2006, pp. 753-760.

Mccord, M.C. et al., "Deep parsing in Watson", IBM J. Res, & Dev. vol. 56 No. 3/4 Paper 3, May/Jul. 2012, pp. 3:1-3:15.

Mcinnes, Bridget T. et al., "UMLS-Interface and UMLA-Similarity: Open Source Software for Measuring Paths and Semantic Similarity", AMIA Symposium Proceedings 2009, Nov. 14, 2009, pp. 431-435.

Pedersen, Ted et al., "WordNet::Similarity—Measuring the Relatedness of Concepts", HLT-NAACL 2004, Demonstration Papers, Boston, Massachusetts, http://www.d.umn.edu/~tpederse/Pubs/AAAI04PedersenT.pdf, May 2, 2004, pp. 1024-1025.

Raghavan, Preethi et al., "Cross-narrative temporal ordering of medical events", Proceedings of the 52nd Annual Meeting of the Association for Computational Linguistics, Baltimore Maryland, Jun. 23-25, 2014, pp. 998-1008.

Sankruthi, Anand, "Event Correlation Technique for Combating Advanced Persistent Threats (APTs)", Symantec Corporation, www.ip.com Prior Art Database Technical Disclosure No. IPCOM000244914D, Jan. 29, 2016, 5 pages.

Saquete, E. et al., "Event Ordering using TERSEO system", Preprint submitted to Elsevier Science, https://pdfs.semanticscholar.org/8220/fdfec9ac7c1fd33539df68eaba9243405ed9.pdf, Feb. 14, 2005, 23 pages.

Sun, Weiyi et al., "Evaluating temporal relations in clinical text: 2012 i2b2 Challenge", Journal of the American Medical Informatics Association, Sep.-Oct. 2013; 20 (5):806-13. doi: 10.1136/amiajnl-2013-001628, Apr. 5, 2013, 8 pages.

Verhagen, Marc et al., "The TempEval Challenge: Identifying Temporal Relations in Text", Language Resources and Evaluation (Impact Factor: 0.62). 43(2), https://www.researchgate.net/publication/220147928_The_tempEval_challenge_Identifying_temporal_relations_in_text, Jun. 2009, 22 pages.

Yuan, Michael J. , "Watson and healthcare, How natural language processing and semantic search could revolutionize clinical decision support", IBM developerWorks, IBM Corporation, Apr. 12, 2011, 14 pages.

Zhou, Li et al., "Temporal reasoning with medical data—A review with emphasis on medical natural language processing", Journal of Biomedical Informatics, vol. 40, Issue 2, Apr. 2007, pp. 183-202.

* cited by examiner

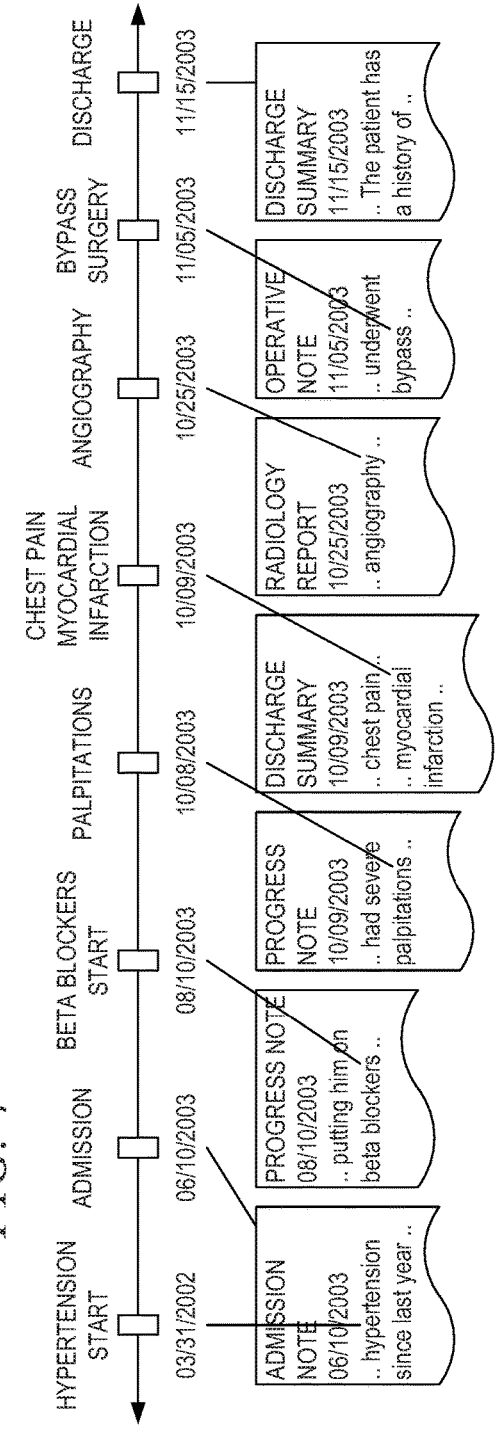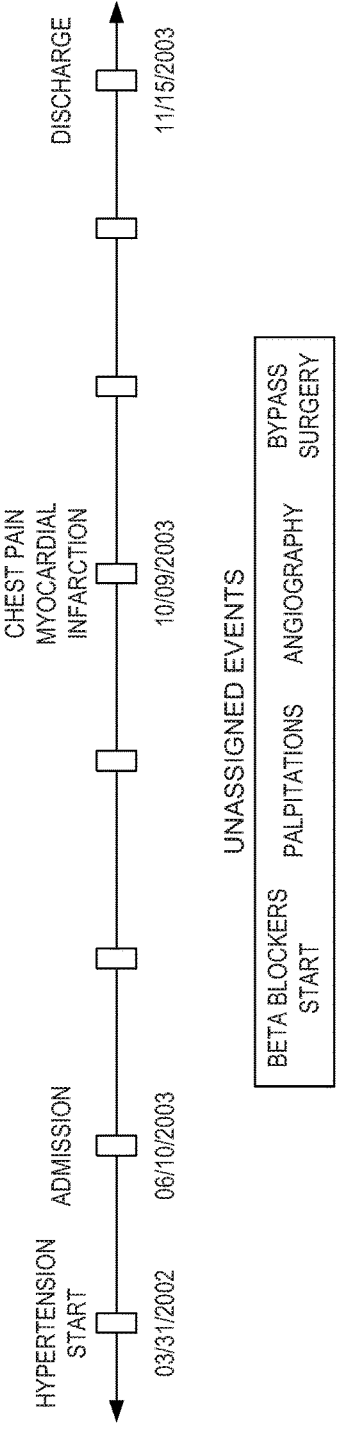

FIG. 6

| EVENT PROGRESSION 1 | EVENT PROGRESSION 2 | EVENT PROGRESSION 3 | EVENT PROGRESSION N |
|---|---|---|---|
| palpitations | angiography | palpitations | blurred vision |
| 2 days (+-1) | 40 days (+-5) | 2 days (+-1) | 0 days (+-1) |
| dizziness | heartburn | nausea | fatigue |
| 5 days (+-2) | 1 days (+-1) | 4 days (+-1) | 0 days (+-1) |
| speech slurring | nausea | dizziness | stroke |
| 1 days (+-1) | 1 days (+-1) | 4 days (+-1) | 1 days (+-1) |
| chest pain | heart attack | chest pain | warfarin |
| 1 days (+-1) | 1 days (+-2) | 1 days (+-1) | 0 days (+-1) |
| myocardial infarction | beta blockers | myocardial infarction | lisinopril |
| ... | ... | ... | ... |

FIG. 7

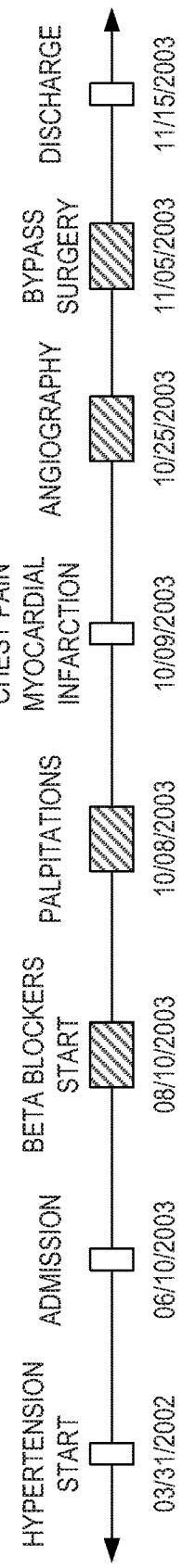

AUTOMATED TIMELINE COMPLETION USING EVENT PROGRESSION KNOWLEDGE BASE

BACKGROUND

The present application relates generally to an improved data processing apparatus and method and more specifically to mechanisms for automated timeline completion using an event progression knowledge base.

With the increased usage of computing networks, such as the Internet, humans are currently inundated and overwhelmed with the amount of information available to them from various structured and unstructured sources. However, information gaps abound as users try to piece together what they can find that they believe to be relevant during searches for information on various subjects. To assist with such searches, recent research has been directed to generating Question and Answer (QA) systems which may take an input question, analyze it, and return results indicative of the most probable answer to the input question. QA systems provide automated mechanisms for searching through large sets of sources of content, e.g., electronic documents, and analyze them with regard to an input question to determine an answer to the question and a confidence measure as to how accurate an answer is for answering the input question.

Examples of QA systems are the IBM Watson™ system available from International Business Machines (IBM®) Corporation of Armonk, N.Y., Siri® from Apple®, and Cortana® from Microsoft®. The IBM Watson™ system is an application of advanced natural language processing, information retrieval, knowledge representation and reasoning, and machine learning technologies to the field of open domain question answering. The IBM Watson™ system is built on IBM's DeepQA™ technology used for hypothesis generation, massive evidence gathering, analysis, and scoring. DeepQA™ takes an input question, analyzes it, decomposes the question into constituent parts, generates one or more hypotheses based on the decomposed question and results of a primary search of answer sources, performs hypothesis and evidence scoring based on a retrieval of evidence from evidence sources, performs synthesis of the one or more hypotheses, and based on trained models, performs a final merging and ranking to output an answer to the input question along with a confidence measure.

Events, and event timelines are an important part of question answering. Knowing the temporal ordering of events described in the text corpus could help DeepQA™ answer questions about these events, such as: "Who became president of the United States in the year 60 Minutes premiered?"

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a computing device configured with instructions executing on a processor of the computing device to implement a timeline generation system for automated timeline completion. The method comprises identifying, by the timeline generation system executing on the processor of the computing device, a plurality of events in documents in a corpus of information. The method further comprises placing, by the timeline generation system, the plurality of events in a partial timeline data structure. The method further comprises selecting, by the timeline generation system, an event progression from an event progression knowledge base. The method further comprises aligning, by the timeline generation system, the selected event progression to the partial timeline data structure. The method further comprises identifying, by the timeline generation system, a set of events missing from the partial timeline data structure. The method further comprises mapping, by the timeline generation system, the set of events missing from the partial timeline data structure to the partial timeline based on the selected event progression to form a completed timeline data structure.

In other illustrative embodiments, a computer program product comprising a computer usable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 4 depicts an example timeline generated from a patient's medical record in accordance with an illustrative embodiment;

FIG. 5 depicts an example partial timeline generated from a patient's medical record with unassigned events in accordance with an illustrative embodiment;

FIG. 6 depicts an example portion of an event progression knowledge base in accordance with an illustrative embodiment;

FIG. 7 depicts an example completed timeline generated from a patient's medical record in accordance with an illustrative embodiment;

DETAILED DESCRIPTION

Figure 1:
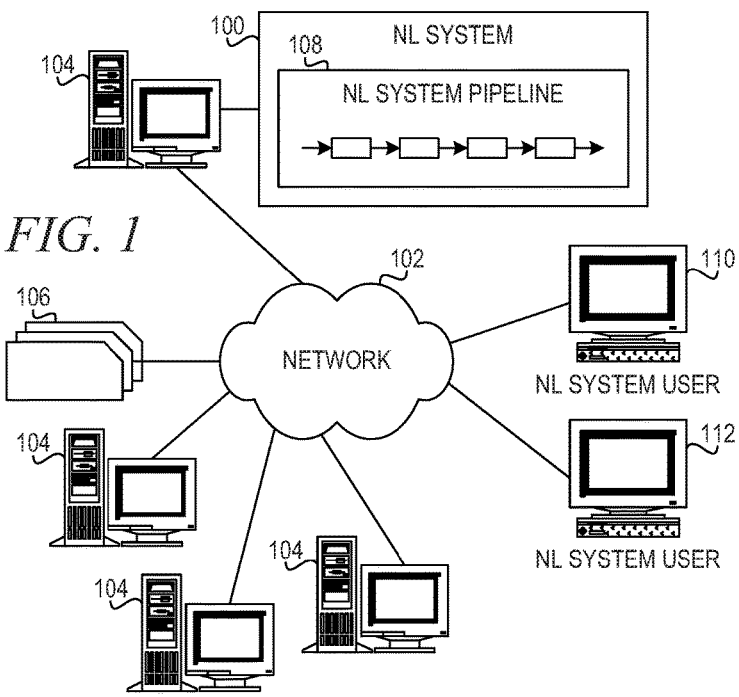
FIG. 1 depicts a schematic diagram of one illustrative embodiment of a natural language processing system in a computer network.

Generating timelines of events from unstructured document sets is an important problem in natural language processing. A timeline displays events in the text in chronological order and provides a useful summary of information in the dataset. Examples include a timeline of medical events from Electronic Medical Records or a timeline of events from news articles. Such timelines have multiple applications in question answering and information retrieval.

However, generating completed timelines of all events in unstructured text is a challenging task as it requires associating every event with any available time information, such as dates, and relatively ordering all events. Often, there is only limited time information available in the document set (e.g., admission and discharge dates on clinical notes); thus, only a subset of events may be easily placed on the timeline leading to a partial timeline data structure. The illustrative embodiments provide an approach to address the problem of partial timeline completion using an event progression knowledge base.

The embodiments are described below with reference to a question answering (QA) system; however, aspects of the illustrative embodiments may apply to other embodiments, such as analytics, data visualization, social media, search engine indexing, etc. Application of aspects of the illustrative embodiments to other embodiments are within the scope of the present invention.

An event timeline data structure is a sequence of chronologically ordered events grounded in time using timestamps.

A partial timeline data structure is an incomplete event timeline with missing events.

An event progression is a natural ordering of events as they typically occur in the real world. An event progression knowledge base is a knowledge resource consisting of multiple event progressions.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 2:
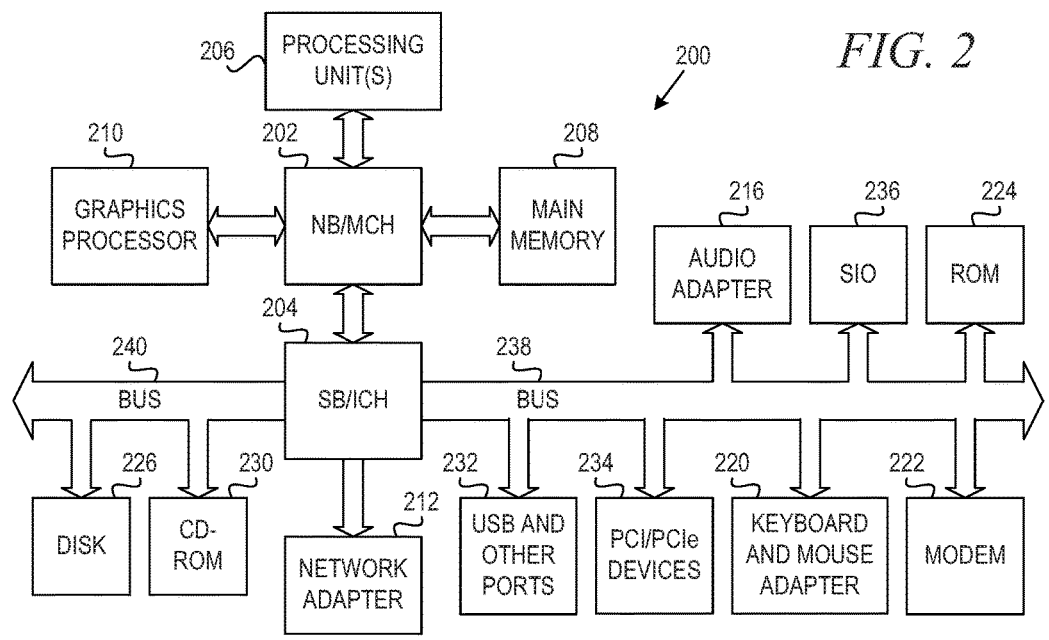
FIG. 2 is a block diagram of an example data processing system in which aspects of the illustrative embodiments are implemented.
Figure 3:
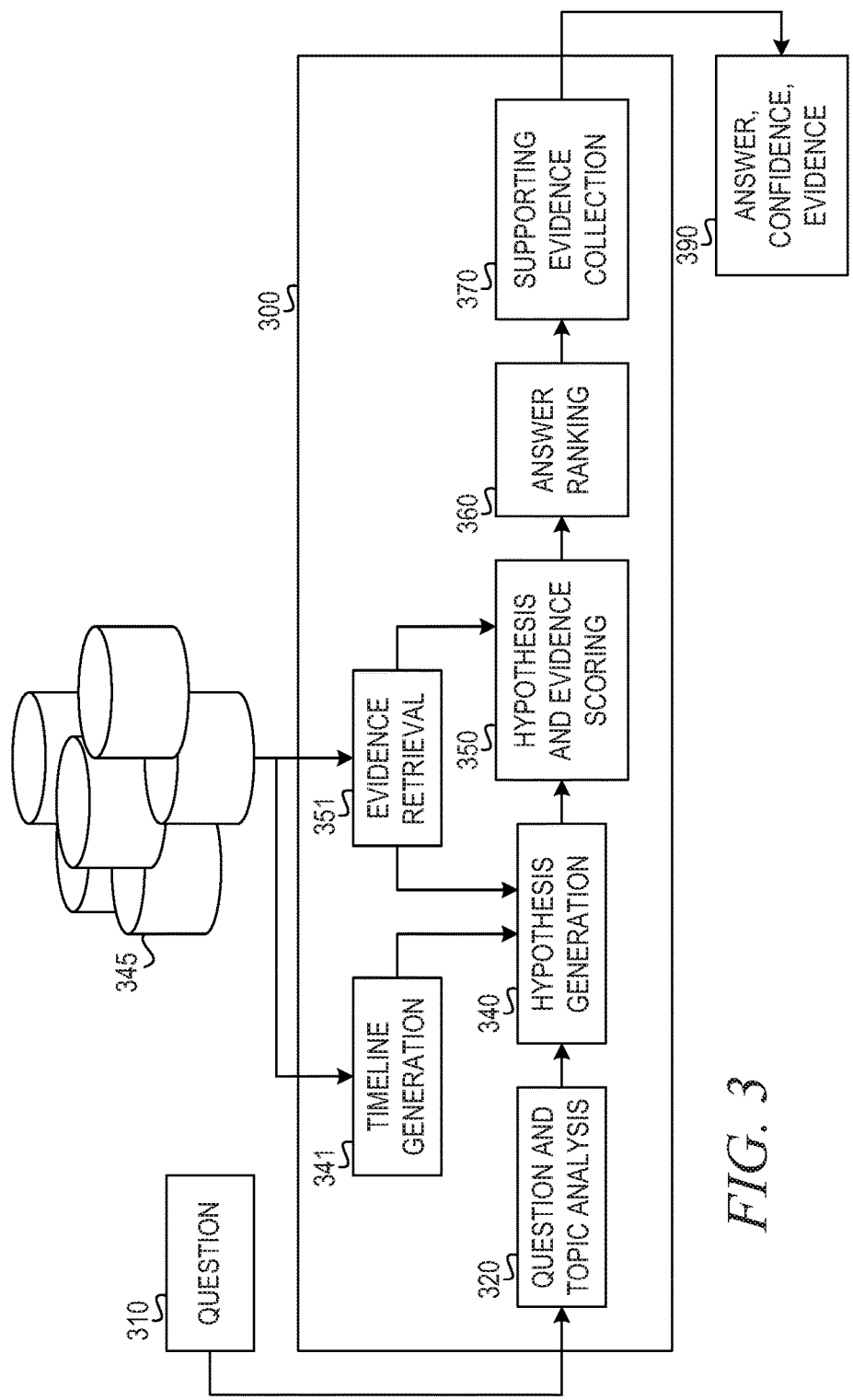
FIG. 3 illustrates a natural language processing system pipeline for processing an input question in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example natural language (NL) processing system, such as a Question Answering (QA) system (also referred to as a Question/Answer system or Question and Answer system), methodology, and computer program product with which the mechanisms of the illustrative embodiments are implemented. As will be discussed in greater detail hereafter, the illustrative embodiments are integrated in, augment, and extend the functionality of these NL processing mechanisms.

With respect to the example embodiment of a QA system, it is important to first have an understanding of how question answering in a QA system is implemented before describing how the mechanisms of the illustrative embodiments are integrated in and augment such QA systems. It should be appreciated that the QA mechanisms described in FIGS. 1-3 are only examples and are not intended to state or imply any limitation with regard to the type of natural language processing mechanisms with which the illustrative embodiments are implemented. Many modifications to the example NL processing system shown in FIGS. 1-3 may be implemented in various embodiments of the present invention without departing from the spirit and scope of the present invention.

As an overview, a Question Answering system (QA system) is an artificial intelligence application executing on data processing hardware that answers questions pertaining to a given subject-matter domain presented in natural language. The QA system receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA system. The document may include any file, text, article, or source of data for use in the QA system. For example, a QA system accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to the QA system which then answers the input questions using the content in the corpus of data by evaluating documents, sections of documents, portions of data in the corpus, or the like. When a process evaluates a given section of a document for semantic content, the process can use a variety of conventions to query such document from the QA system, e.g., sending the query to the QA system as a well-formed question which is then interpreted by the QA system and providing a response containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA system receives an input question, analyzes the question to extract the major elements of the question, uses the extracted element to formulate queries, and then applies those queries to the corpus of data. Based on the application of the queries to the corpus of data, the QA system generates a set of hypotheses, or candidate answers to the input question, by looking across the corpus of data for portions of the corpus of data that have some potential for containing a valuable response to the input question. The QA system then performs deep analysis, e.g., English Slot Grammar (ESG) and Predicate Argument Structure (PAS) builder, on the language of the input question and the language used in each of the portions of the corpus of data found during the application of the queries using a variety of scoring algorithms. There may be hundreds or even thousands of scoring algorithms applied, each of which performs different analysis, e.g., comparisons, natural language analysis, lexical analysis, or the like, and generates a score. For example, some scoring algorithms may look at the matching of terms and synonyms within the language of the input question and the found portions of the corpus of data. Other scoring algorithms may look at temporal or spatial features in the language, while others may evaluate the source of the portion of the corpus of data and evaluate its veracity.

The scores obtained from the various scoring algorithms indicate the extent to which the potential response is likely to be a correct answer to the input question based on the specific area of focus of that scoring algorithm. Each resulting score is then weighted against a statistical model, which is used to compute the confidence that the QA system has regarding the evidence for a candidate answer being the correct answer to the question. This process is repeated for each of the candidate answers until the QA system identifies candidate answers that surface as being significantly stronger than others and thus, generates a final answer, or ranked set of answers, for the input question.

As mentioned above, QA systems and mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, etc.). Conventional question answering systems are capable of generating answers based on the corpus of data and the input question, verifying answers to a collection of questions from the corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA system to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA system. Content creators, automated tools, or the like, annotate or otherwise generate metadata for providing information usable by the QA system to identify these question-and-answer attributes of the content.

Operating on such content, the QA system generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a natural language processing system 100 in a computer network 102. One example of a question/answer generation, which may be used in conjunction with the principles described herein, is described in U.S. Patent Application Publication No. 2011/0125734, which is herein incorporated by reference in its entirety. The NL processing system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. In the depicted example, NL processing system 100 and network 102 enables question answering functionality for one or more QA system users via their respective computing devices 110-112. Other embodiments of the NL processing system 100 may be used with components, systems, subsystems, and/or devices other than those that are depicted herein.

The NL processing system 100 is configured to implement an NL system pipeline 108 that receives inputs from various sources. For example, the NL processing system 100 receives input from the network 102, a corpus of electronic documents 106, NL system users, and/or other data and other possible sources of input. In one embodiment, some or all of the inputs to the NL processing system 100 are routed through the network 102. The various computing devices 104 on the network 102 include access points for content creators and NL system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the NL processing system 100 may operate in environments of any size, including local and global, e.g., the Internet.

In one embodiment, the content creator creates content in a document of the corpus of data 106 for use as part of a corpus of data with the NL processing system 100. The document includes any file, text, article, or source of data for use in the NL processing system 100. NL system users access the NL processing system 100 via a network connection or an Internet connection to the network 102, and input questions to the NL processing system 100 that are answered by the content in the corpus of data 106. In one embodiment, the questions are formed using natural language. The NL processing system 100 analyzes and interprets the question, and provides a response to the NL system user, e.g., NL processing system user 110, containing one or more answers to the question. In some embodiments, the NL processing system 100 provides a response to users in a ranked list of candidate answers while in other illustrative embodiments, the NL processing system 100 provides a single final answer or a combination of a final answer and ranked listing of other candidate answers.

The NL processing system 100 implements NL system pipeline 108, which comprises a plurality of stages for processing an input question and the corpus of data 106. The NL processing system pipeline 108 generates answers for the input question based on the processing of the input question and the corpus of data 106. The NL processing system pipeline 108 will be described in greater detail hereafter with regard to FIG. 3.

In some illustrative embodiments, the NL processing system 100 may be the IBM Watson™ QA system available from International Business Machines Corporation of Armonk, N.Y., which is augmented with the mechanisms of the illustrative embodiments described hereafter. As outlined previously, the IBM Watson™ QA system receives an input question, which it then analyzes to extract the major features of the question, that in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The IBM Watson™ QA system then performs deep analysis on the language of the input question and the language used in each of the portions of the corpus of data found during the application of the queries using a variety of scoring algorithms. The scores obtained from the various scoring algorithms are then weighted against a statistical model that summarizes a level of confidence that the IBM Watson™ QA system has regarding the evidence that the potential response, i.e. candidate answer, is inferred by the question. This process is repeated for each of the candidate answers to generate ranked listing of candidate answers which may then be presented to the user that submitted the input question, or from which a final answer is selected and presented to the user. More information about the IBM Watson™ QA system may be obtained, for example, from the IBM Corporation website, IBM Redbooks, and the like. For example, information about the IBM Watson™ QA system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements an NL processing system 100 and NL system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java® programs or applications executing on data processing system 200.

As a server, data processing system 200 may be, for example, an IBM® eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 illustrates a natural language processing system pipeline for processing an input question in accordance with one illustrative embodiment. The natural language (NL) processing system pipeline of FIG. 3 may be implemented, for example, as NL system pipeline 108 of NL processing system 100 in FIG. 1. It should be appreciated that the stages of the NL processing system pipeline shown in FIG. 3 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The NL system pipeline of FIG. 3 is augmented, for example, in one or more of the stages to implement the improved mechanism of the illustrative embodiments described hereafter, additional stages may be provided to implement the improved mechanism, or separate logic from the pipeline 300 may be provided for interfacing with the pipeline 300 and implementing the improved functionality and operations of the illustrative embodiments.

In the depicted example, NL system pipeline 300 is implemented in a Question Answering (QA) system. The description that follows refers to the NL system pipeline or the NL system pipeline as a QA system; however, aspects of the illustrative embodiments may be applied to other NL processing systems, such as Web search engines that return semantic passages from a corpus of documents.

As shown in FIG. 3, the NL system pipeline 300 comprises a plurality of stages 310-390 through which the NL system operates to analyze an input question and generate a final response. In an initial question input stage, the NL system receives an input question 310 that is presented in a natural language format. That is, a user inputs, via a user interface, an input question 310 for which the user wishes to obtain an answer, e.g., "Who were Washington's closest advisors?" In response to receiving the input question 310, the next stage of the NL system pipeline 300, i.e. the question and topic analysis stage 320, analyzes the input question using natural language processing (NLP) techniques to extract major elements from the input question, and classify the major elements according to types, e.g., names, dates, or any of a plethora of other defined topics. For example, in the example question above, the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic.

In addition, the extracted major features include key words and phrases classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of attention deficit disorder with relatively few side effects?," the focus is "What drug" since if this phrase were replaced with the answer it would generate a true sentence, e.g., the answer "Adderall" can be used to replace the phrase "What drug" to generate the sentence "Adderall has been shown to relieve the symptoms of attention deficit disorder with relatively few side effects." The focus often, but not always, contains the LAT. On the other hand, in many cases it is not possible to infer a meaningful LAT from the focus.

Referring again to FIG. 3, the identified major elements of the question are then used during a hypothesis generation stage 340 to decompose the question into one or more search queries that are applied to the corpora of data/information 345 in order to generate one or more hypotheses. The queries are applied to one or more text indexes storing information about the electronic texts, documents, articles, websites, and the like, that make up the corpus of data/information, e.g., the corpus of data 106 in FIG. 1. The queries are applied to the corpus of data/information at the hypothesis generation stage 340 to generate results identifying potential hypotheses for answering the input question, which can then be evaluated. That is, the application of the queries results in the extraction of portions of the corpus of data/information matching the criteria of the particular query. These portions of the corpus are then analyzed and used in the hypothesis generation stage 340, to generate hypotheses for answering the input question 310. These hypotheses are also referred to herein as "candidate answers" for the input question. For any input question, at this stage 340, there may be hundreds of hypotheses or candidate answers generated that may need to be evaluated.

The queries and hypotheses generated by hypothesis generation phase 340 may be time-based. Thus, a timeline of events derived from documents in corpora 345 is an important aspect of NL system pipeline 300. Timeline generation component 341, or timeline generation system, analyzes documents in corpora 345 to identify events and place the identified events in a timeline. Timeline generation component 341 also consults an event progression knowledge base (not shown) to determine whether there are any events missing from the unstructured documents in corpora 345. Events may be missing because they are not properly documented or they are not recognizable through the NL processing of NL system pipeline 300.

Timeline generation component 341 matches and aligns event progressions from event progression knowledge base to the partial timeline data structure (with missing events) and finds the best alignment between the event progressions and the partial timeline data structure. Timeline generation component 341 then identifies missing events from the identified best alignment and matches the missing events from the missing event set to the selected event progression. Timeline generation component 341 then maps the matched missing events to the partial timeline data structure to generate a completed timeline data structure. The completed timeline data structure is then available for queries from hypotheses generation stage 340.

In an alternative embodiment, timeline generation component 341 may generate a completed timeline as part of pre-processing of documents in corpora 345 rather than in response to receiving a particular input question 310. Timeline generation component 341 may generate completed timelines from events identified in documents in corpora 345 and then store the completed timelines in corpora 345. Those completed timelines in corpora 345 would then be available for queries from hypothesis generation stage 340 during run-time processing of questions.

The NL system pipeline 300, in stage 350, then performs a deep analysis and comparison of the language of the input question and the language of each hypothesis or "candidate answer," as well as performs evidence scoring to evaluate the likelihood that the particular hypothesis is a correct answer for the input question. This involves evidence retrieval 351, which retrieves passages from corpora 345. Hypothesis and evidence scoring phase 350 uses a plurality of scoring algorithms, each performing a separate type of analysis of the language of the input question and/or content of the corpus that provides evidence in support of, or not in support of, the hypothesis. Each scoring algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In general, however, these algorithms look for particular terms, phrases, or patterns of text that are indicative of terms, phrases, or patterns of interest and determine a degree of matching with higher degrees of matching being given relatively higher scores than lower degrees of matching.

For example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that this is just one simple example of how scoring can be performed. Many other algorithms of various complexities may be used to generate scores for candidate answers and evidence without departing from the spirit and scope of the present invention.

In answer ranking stage 360, the scores generated by the various scoring algorithms are synthesized into confidence scores or confidence measures for the various hypotheses. This process involves applying weights to the various scores, where the weights have been determined through training of the statistical model employed by the QA system and/or dynamically updated. For example, the weights for scores generated by algorithms that identify exactly matching terms and synonyms may be set relatively higher than other algorithms that evaluate publication dates for evidence passages.

The weighted scores are processed in accordance with a statistical model generated through training of the QA system that identifies a manner by which these scores may be combined to generate a confidence score or measure for the individual hypotheses or candidate answers. This confidence score or measure summarizes the level of confidence that the QA system has about the evidence that the candidate answer is inferred by the input question, i.e. that the candidate answer is the correct answer for the input question.

The resulting confidence scores or measures are processed by answer ranking stage 360, which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers").

Supporting evidence collection phase 370 collects evidence that supports the candidate answers from answer ranking phase 360. From the ranked listing of candidate answers in stage 360 and supporting evidence from supporting evidence collection stage 370, NL system pipeline 300 generates a final answer, confidence score, and evidence 380, or final set of candidate answers with confidence scores and supporting evidence, and outputs answer, confidence, and evidence 390 to the submitter of the original input question 310 via a graphical user interface or other mechanism for outputting information.

FIG. 4 depicts an example timeline generated from a patient's medical record in accordance with an illustrative embodiment. The timeline represented in FIG. 4 displays events in the text of documents in chronological order that are critical to natural language understanding. In the depicted example, the documents include a admission notes, progress notes, discharge summaries, a radiology report, and an operative note. These documents are dated, providing time information that can be aligned with a timeline. These documents also include other event information, such as hypertension start, beta blockers start, palpitations, chest pain, myocardial infarction, angiography, and bypass surgery.

Automated timeline generation from large unstructured document sets provides a useful summary of information in the dataset. Automated timeline generation also has many other applications, including question answering and information retrieval. For example, given the timeline of FIG. 4, a QA system may receive the following question: "Was the patient on beta blockers before the cardiac incident?" As another example, in information retrieval, the following search query may be generated: "beta blockers before myocardial infarction."

Often, there may be limited information available in the text to assign timestamps to events and place them on the timeline. Examples of event timestamp information may include document creation date, such as news article publication date, admission and discharge dates in case of clinical notes, and any other explicit mentions of dates that can be associated with events. Thus, only the subset of events that can be associated with explicit dates in the text may be placed on the timeline, leading to an incomplete or partial timeline data structure.

FIG. 5 depicts an example partial timeline generated from a patient's medical record with unassigned events in accordance with an illustrative embodiment. In the depicted example, hypertension start, admission, chest pain and myocardial infarction, and discharge have explicit dates allowing them to be placed on the timeline. However, beta blockers start, palpitations, angiography, and bypass surgery lack time information in the document text and, hence, are not mapped to the timeline.

The mechanisms of the illustrative embodiments use general timelines of events as they naturally occur in the real world to help complete partial timelines. These timelines are referred to herein as event progressions. Event progressions may be created by domain experts, such as physicians. For example, even progressions may be created for disease progressions in the medical domain, progressions for critical weather events like cyclones and tornados, or news event progression. Each event in the event progression has the following time information: rank information implicit in the ordering, approximate distance from the next event, and confidence or fuzziness factor for the distance.

FIG. 6 depicts an example portion of an event progression knowledge base in accordance with an illustrative embodiment. In event progression 1, the first event is palpitations with 2 days (plus or minus one day) to the next event, which is dizziness with 5 days (plus or minus 2 days) to the next event, and so on. Each event progression is an example timeline of events created by a subject matter expert or learned from a large corpus using machine learning.

The mechanisms of the illustrative embodiments may aggregate document-specific ordering decisions across the corpus to estimate a generalized order. The mechanisms may count the number of times two events are locally classified as before or after. If the number of before relations classified in the corpus is significantly greater than after, a schema can order those two events and add them to a progression.

The illustrative embodiments provide mechanisms for partial timeline completion using an event progression knowledge base. The mechanisms assign timestamps to missing events and place them in appropriate positions on the timeline. FIG. 7 depicts an example completed timeline generated from a patient's medical record in accordance with an illustrative embodiment.

Figure 8:
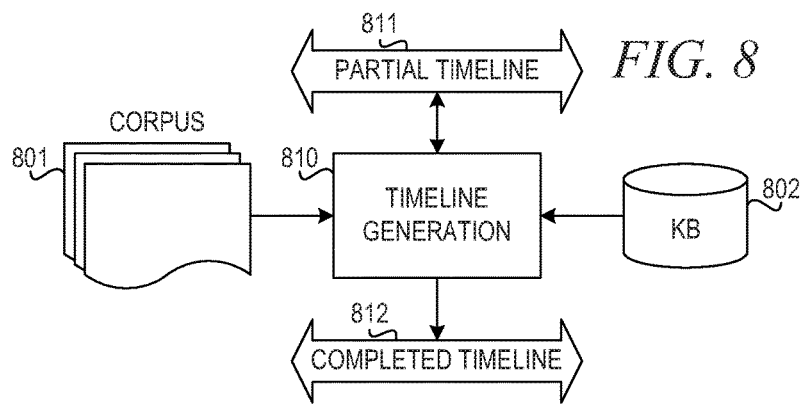
FIG. 8 is a block diagram illustrating a timeline generation system for completing a partial timeline in accordance with an illustrative embodiment.

FIG. 8 is a block diagram illustrating a timeline generation system for completing a partial timeline in accordance with an illustrative embodiment. Timeline generation system 810 analyzes structured or unstructured documents in corpus 801 to identify events that can be placed in partial timeline data structure 811. Timeline generation system 810 also identifies events missing from partial timeline data structure 811 based on an event progression knowledge base 802 to form a missing event set.

Figure 9:
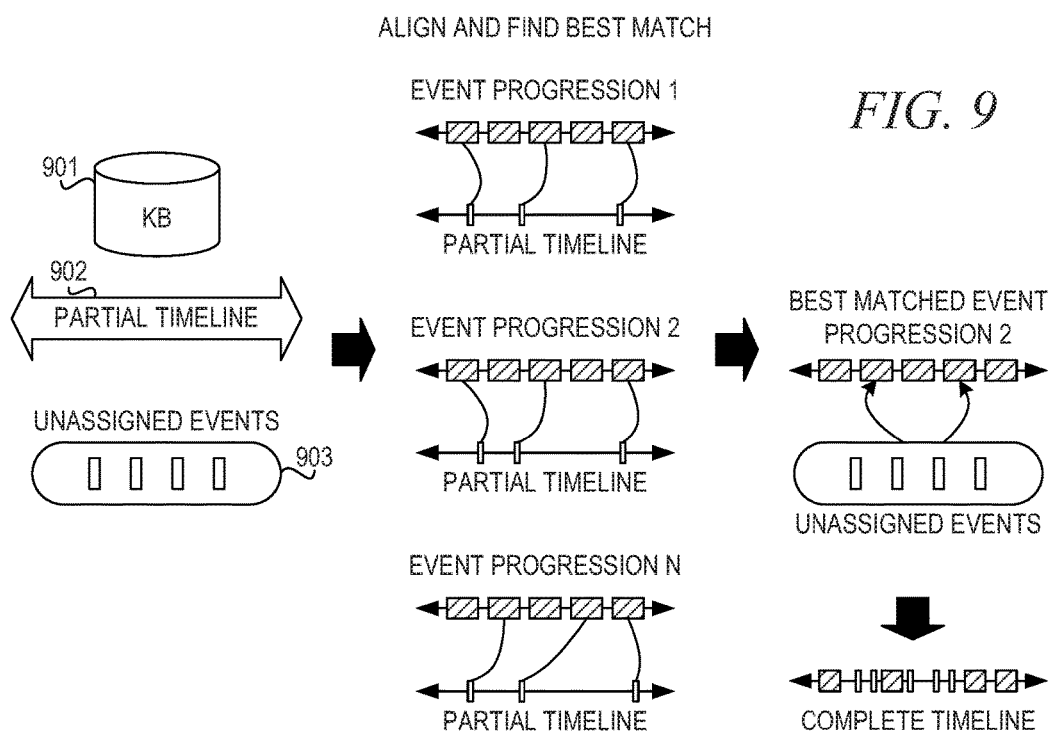
FIG. 9 illustrates the operation of a timeline generation system matching unassigned events to a partial timeline in accordance with an illustrative embodiment.

FIG. 9 illustrates the operation of a timeline generation component matching unassigned events to a partial timeline in accordance with an illustrative embodiment. Timeline generation system 810 matches and aligns event progressions from knowledge base 802 (902 in FIG. 9) to partial timeline data structure 811 (901 in FIG. 9). Timeline generation system 810 selects a best alignment between the event progressions and partial timeline data structure 811. In the example shown in FIG. 9, even progression 2 is identified as the best matched event progression. Timeline generation system 810 then identifies the missing events from the selected event progression. Timeline generation system 810 also matches events from the missing event set (unassigned events 903 in FIG. 9) to the selected event progression. Timeline generation system 810 maps the matched missing events to partial timeline data structure 811 to form completed timeline data structure 812.

The timeline generation system 810 uses an event progression knowledge base to estimate time information for events missing from the timeline to automatically complete the timeline. A mapping function finds the event progressions in the knowledge base that best matches the partial timeline. The timeline generation system 810 finds the best alignment between the selected event progression and the partial timeline.

The mapping function also matches events from the missing event set to the selected event progression. The mapping function maps the matched missing events to the partial timeline by leveraging the temporal information in the event progression to establish the position and date of the missing events in the partial timeline.

More specifically, the mapping function matches all event progressions in the knowledge base with the partial timeline. The mapping function outputs a similarity score between every two events across the event progression and partial timeline. For example, a simple mapping function may output a score of 1 for identical and synonymous events and a score of 0 otherwise.

Map(myocardial infarction$_{eventprogression}$,heart attack$_{partialtimeline}$)=1

Map(dizziness$_{eventprogression}$,chest pain$_{partialtimeline}$)=0

The similarity of events is calculated using a knowledge-based approach by leveraging ontologies, such as Unified Medical Language System (UMLS) or Wordnet. The Unified Medical Language System (UMLS) is a compendium of many controlled vocabularies in the biomedical sciences. It provides a mapping structure among these vocabularies and thus allows one to translate among the various terminology systems. It may also be viewed as a comprehensive thesaurus and ontology of biomedical concepts. UMLS further provides facilities for natural language processing. It is intended to be used mainly by developers of systems in medical informatics WordNet is a lexical database for the English language. It groups English words into sets of synonyms called synsets, provides short definitions and usage examples, and records a number of relations among these synonym sets or their members. WordNet can thus be seen as a combination of dictionary and thesaurus. While it is accessible to human users via a web browser, its primary use is in automatic text analysis and artificial intelligence applications. The mapping function locates the concept in the ontology; concepts that map to the same identifier are considered synonymous.

The timeline generation system 810 of the illustrative embodiments leverages the scores produced by the mapping function to align all event progressions against the partial timeline data structure. For alignment, popular dynamic programming algorithms, such as Needleman Wunsch or Smith Waterman, may be used. The timeline generation system 810 picks the highest scoring alignment as the best match. Alternately, the timeline generation system 810 may pick the top N alignments as the bets matched event progressions.

The timeline generation system 810 also uses a mapping function to map events in the missing event set to the events in the best progression. The mapping function is based on the semantic similarity or synonymity between event pairs. Semantic similarity may be calculated with knowledge-based resources, such as UMLS or WordNet.

For each unassigned event mapped to the event progression, the timeline generation system 810 leverages available time information to estimate the relative position of the missing event in the partial timeline. In the example depicted in FIGS. 4-7, the missing event palpitations maps to the palpitations event in the progression. The timeline generation system 810 checks rank and distance of the event in the progression. The timeline generation system 810 estimates a position and score for placing each missing event on the partial timeline data structure:

Position_Finder(Relative Rank,Distance,Confidence Interval)=Score

Consider the unassigned event "palpitation" maps to "palpitation" in the selected event progression. From the event progression, the timeline generation system 810 learns that "palpitation" occurs two days after "dizziness," and one day before "chest pain." Using this time information, the timeline generation system 810 may find that "dizziness" and "chest pain" on the partial timeline and place "palpitations" approximately two days after "dizziness" and one day before "chest pain" in the partial timeline. The timeline generation system 810 repeats this process for all unassigned events until a completed timeline data structure is generated.

The mapping functions calculate similarity using knowledge-based methods. Machine learning methods that incorporate features obtained through knowledge-driven and distributional methods may be used to calculate similarity. The matching and alignment problem can be extended as follows:

all permutations of missing events are placed in the partial timeline data structure to generate multiple candidate timelines;

align and score each candidate with each event progression;

pick the alignment pair of (Event Progression, Candidate) with maximum score.

The timeline generation system 810 may pick the top N aligned event progressions and use information from across those N progressions to complete the partial timeline.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 10:
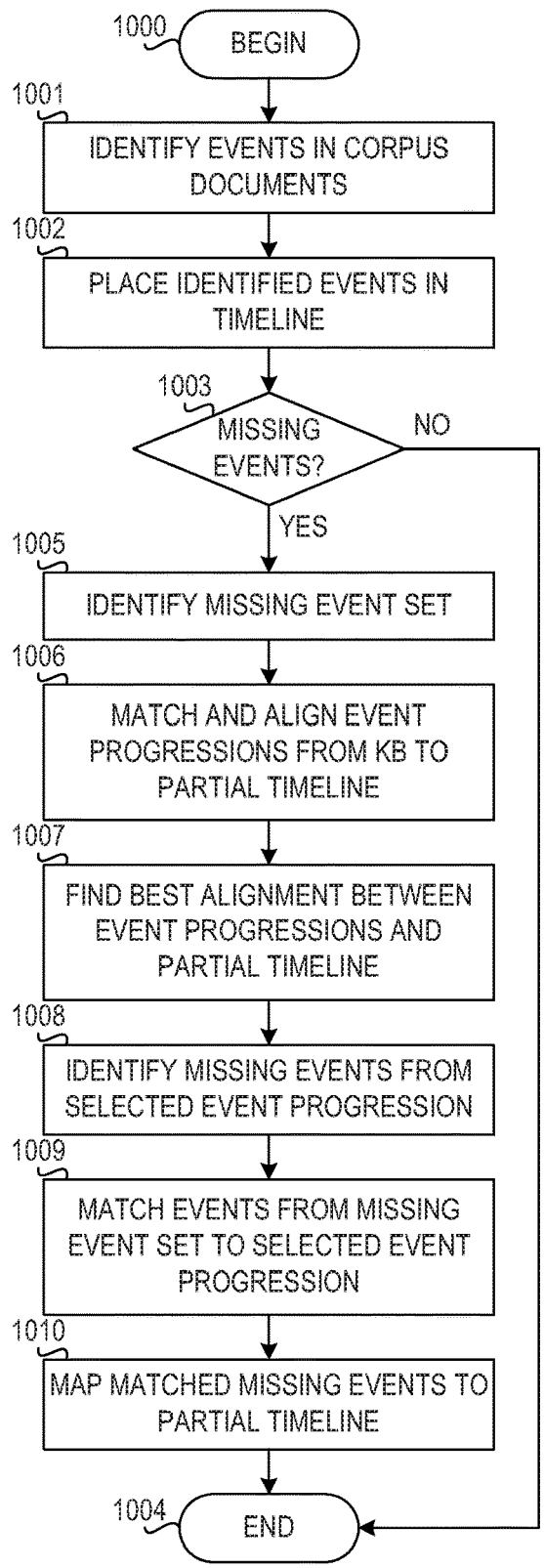
FIG. 10 is a flowchart illustrating operation of a timeline generation system in accordance with an illustrative embodiment.

FIG. 10 is a flowchart illustrating operation of a timeline generation component in accordance with an illustrative embodiment. Operation begins (block 1000), and the timeline generation component identifies events in a corpus of documents (block 1001). The timeline generation component places the identified events in a timeline (block 1002). The timeline generation component determines whether events are missing from the timeline, i.e., a partial timeline data structure (block 1003). Events may be missing if there are events without explicit time information or if events occur in an event progression in a knowledge base that do not occur in the timeline. If the timeline generation component determines there are no missing events, then operation ends (block 1004).

If the timeline generation component determines there are missing events in the timeline in block 1003, then the timeline generation component identifies the missing event set (1005). The timeline generation component matches and aligns events progressions from an event progressions knowledge base to the partial timeline data structure (block 1006). The timeline generation component finds the best alignment between the event progressions and partial timeline data structure to select a particular event progression (block 1007).

The timeline generation component then identifies missing events from the selected event progression (block 1008) and matches events from the missing event set to the selected event progression (block 1009). The timeline generation component maps the matched missing events to the partial timeline data structure to form a completed timeline data structure (block 1010). Thereafter, operation ends (block 1004).

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide a mechanism for generating a completed timeline based on structured and unstructured documents in a corpus and an event progression knowledge base. The illustrative embodiments are directly applicable to resolving temporal constraints and event changes in a question answering system. Assets generated by such a system would be useful in any use case requiring understanding of temporal relations (question answering, summarization, search, etc.). Examples of use of such timeline completion include any domain with multiple documents and few dates to ground events. Aspects of the illustrative embodiments also apply to passage scoring components of a question answering system. The timeline generation component of the illustrative embodiments is a fully automated approach for leveraging an event progression knowledge base for timeline completion and requires easily available algorithms and resources.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a computing device configured with instructions executing on a processor of the computing device to implement a natural language processing system, for automated timeline completion, the method comprising:
    identifying, by a timeline generation component executing within a natural language processing pipeline of the natural language processing system, a plurality of events having time information in documents in a corpus of information;
    placing, by the timeline generation component, the plurality of events in a partial timeline data structure;
    selecting, by the timeline generation component, an event progression from an event progression knowledge base, wherein the event progression knowledge base is a knowledge resource consisting of multiple event progressions, wherein each event progression in the event progression knowledge base is a natural ordering of a sequence of events as they typically occur in the real world, and wherein each event in a given event progression has the following time information: rank information implicit in the ordering, approximate distance from the next event, and confidence or fuzziness factor for the distance, wherein selecting the event progression from the event progression knowledge base comprises:
        aligning each event progression in the event progression knowledge base to the partial timeline data structure;
        determining a matching score of each event progression based on a mapping function; and
        selecting an event progression having a highest matching score;
    aligning, by the timeline generation component, the selected event progression to the partial timeline data structure;
    identifying, by the timeline generation component, a set of events present in the selected event progression and missing from the partial timeline data structure;
    identifying, by the timeline generation component, a set of unassigned events in the documents in the corpus that lack associated time information and are not placed the partial timeline data structure;
    matching, by the timeline generation component, the set of unassigned events to the selected event progression based on semantic similarity or synonymity between event pairs to form a set of matched unassigned events;
    mapping, by the timeline generation component, the set of matched events to the partial timeline based on the selected event progression to form a completed timeline data structure including the plurality of events having time information and the set of matched events;
    storing, by the timeline generation component, the completed timeline data structure in the corpus of information; and
    performing by the natural language processing system, a time-based natural language processing operation using the completed timeline data structure and the corpus of information.

2. The method of claim 1, wherein identifying the plurality of events comprises performing natural language processing on unstructured documents in the corpus of information.

3. The method of claim 1, wherein the mapping function outputs a similarity score between events across the event progression and the partial timeline data structure.

4. The method of claim 3, wherein the mapping function outputs a similarity score of 1 if an event in the event progression and an event in the partial timeline data structure are identical or synonymous and outputs a similarity score of 0 if the event in the event progression and the event in the partial timeline data structure are not identical or synonymous.

5. The method of claim 4, wherein the mapping function determines a similarity score using a knowledge-based approach based on an ontology data structure.

6. The method of claim 1, wherein aligning each event progression in the event progression knowledge base to the partial timeline data structure comprises aligning each event progression in the event progression knowledge base to the partial timeline data structure using a dynamic programming algorithm.

7. The method of claim 1, wherein mapping the set of events missing from the partial timeline data structure to the partial timeline comprises matching the set of events missing from the partial timeline data structure to the selected event progression based on semantic similarity or synonymity between event pairs.

8. The method of claim 7, wherein semantic similarity is calculated using a knowledge-based approach based on an ontology data structure.

9. The method of claim 1, wherein performing the time-based processing comprises performing question answering in a natural language system pipeline executing within the natural language processing system.

10. A computer program product comprising a computer readable storage medium having a computer readable program stored therein, wherein the computer readable program comprises instructions, which when executed on a processor of a computing device causes the computing device to implement a timeline generation system for automated timeline completion, wherein the computer readable program causes the computing device to:
  identify, by a timeline generation component executing within a natural language processing pipeline of the natural language processing system, a plurality of events having time information in documents in a corpus of information;
  place, by the timeline generation component, the plurality of events in a partial timeline data structure;
  select, by the timeline generation component, an event progression from an event progression knowledge base, wherein the event progression knowledge base is a knowledge resource consisting of multiple event progressions, wherein each event progression in the event progression knowledge base is a natural ordering of a sequence of events as they typically occur in the real world, and wherein each event in a given event progression has the following time information: rank information implicit in the ordering, approximate distance from the next event, and confidence or fuzziness factor for the distance, wherein selecting the event progression from the event progression knowledge base comprises:
    aligning each event progression in the event progression knowledge base to the partial timeline data structure;
    determining a matching score of each event progression based on a mapping function; and
    selecting an event progression having a highest matching score;
  align, by the timeline generation component, the selected event progression to the partial timeline data structure;
  identify, by the timeline generation component, a set of events present in the selected event progression and missing from the partial timeline data structure;
  identify, by the timeline generation component, a set of unassigned events in the documents in the corpus that lack associated time information and are not placed the partial timeline data structure;
  match, by the timeline generation component, the set of unassigned events to the selected event progression based on semantic similarity or synonymity between event pairs to form a set of matched unassigned events;
  map, by the timeline generation component, the set of matched events to the partial timeline based on the selected event progression to form a completed timeline data structure including the plurality of events having time information and the set of matched events;
  store, by the timeline generation component, the completed timeline data structure in the corpus of information; and
  perform, by the natural language processing system, a time-based natural language processing operation using the completed timeline data structure and the corpus of information.

11. The computer program product of claim 10, wherein the mapping function outputs a similarity score between events across the event progression and the partial timeline data structure.

12. A computing device comprising:
  a processor; and
  a memory coupled to the processor, wherein the memory comprises instructions, which when executed on a processor of a computing device causes the computing device to implement a timeline generation system for automated timeline completion, wherein the instructions cause the processor to:
  identify, by a timeline generation component executing within a natural language processing pipeline of the natural language processing system, a plurality of events having time information in documents in a corpus of information;
  place, by the timeline generation component, the plurality of events in a partial timeline data structure;
  select, by the timeline generation component, an event progression from an event progression knowledge base, wherein the event progression knowledge base is a knowledge resource consisting of multiple event progressions, wherein each event progression in the event progression knowledge base is a natural ordering of a sequence of events as they typically occur in the real world, and wherein each event in a given event progression has the following time information: rank information implicit in the ordering, approximate distance from the next event, and confidence or fuzziness factor for the distance, wherein selecting the event progression from the event progression knowledge base comprises:
    aligning each event progression in the event progression knowledge base to the partial timeline data structure;
    determining a matching score of each event progression based on a mapping function; and
    selecting an event progression having a highest matching score;

align, by the timeline generation component, the selected event progression to the partial timeline data structure;

identify, by the timeline generation component, a set of events present in the selected event progression and missing from the partial timeline data structure;

identify, by the timeline generation component, a set of unassigned events in the documents in the corpus that lack associated time information and are not placed the partial timeline data structure;

match, by the timeline generation component, the set of unassigned events to the selected event progression based on semantic similarity or synonymity between event pairs to form a set of matched unassigned events;

map, by the timeline generation component, the set of matched events to the partial timeline based on the selected event progression to form a completed timeline data structure including the plurality of events having time information and the set of matched events;

store, by the timeline generation component, the completed timeline data structure in the corpus of information; and perform, by the natural language processing system, a time-based natural language processing operation using the completed timeline data structure and the corpus of information.

13. The computing device of claim 12, wherein the mapping function outputs a similarity score between events across the event progression and the partial timeline data structure.

14. The computing device of claim 13, wherein the mapping functions outputs a similarity score of 1 if an event in the event progression and an event in the partial timeline data structure are identical or synonymous and outputs a similarity score of 0 if the event in the event progression and the event in the partial timeline data structure are not identical or synonymous.

* * * * *